United States Patent [19]

Noiles

[11] 4,340,050
[45] Jul. 20, 1982

[54] MEDICAL FLUID FLOW RATE INDICATING/CONTROLLING DEVICE

[75] Inventor: Douglas G. Noiles, New Canaan, Conn.

[73] Assignee: Delmed Inc., Canton, Mass.

[21] Appl. No.: 220,831

[22] Filed: Dec. 29, 1980

[51] Int. Cl.³ .............................................. A61M 5/14
[52] U.S. Cl. ............................ 128/214 C; 128/214 R; 137/571; 137/426; 137/454; 222/160
[58] Field of Search .......... 128/214 R, 214 B, 214 C, 128/214 D, 214 E, 214 F, 225, 227, DIG. 12, DIG. 13, DIG. 16; 137/571, 576, 426, 454, 433; 251/205; 222/55, 67–69, 160

[56] References Cited

U.S. PATENT DOCUMENTS

| | | |
|---|---|---|
| 1,205,410 | 11/1916 | Tenney . |
| 1,338,782 | 5/1920 | Lindahl . |
| 1,427,455 | 8/1922 | Gates . |
| 1,844,342 | 2/1932 | Berman . |
| 2,090,273 | 8/1937 | Wagner ................... 137/68 |
| 2,254,833 | 9/1941 | Ashkenaz ................ 128/213 |
| 2,479,786 | 8/1949 | Stevens .................... 73/216 |
| 2,865,534 | 12/1958 | Barnes ...................... 222/66 |
| 2,954,028 | 9/1960 | Smith ...................... 128/214 |
| 2,971,366 | 2/1961 | Tomkow ..................... 73/3 |
| 2,989,052 | 6/1961 | Broman .................... 128/214 |
| 3,001,397 | 9/1961 | Leonard ..................... 73/194 |
| 3,017,885 | 1/1962 | Robicsek .................. 128/214 |
| 3,034,504 | 5/1962 | Winsor et al. ............. 128/214 |
| 3,037,384 | 6/1962 | Good ........................ 73/211 |
| 3,049,918 | 8/1962 | Sparkuhl .................... 73/209 |
| 3,101,710 | 8/1963 | Koehn ...................... 128/214 |
| 3,157,481 | 11/1964 | Bujan ....................... 55/417 |
| 3,166,107 | 1/1965 | Swenson et al. .......... 141/145 |
| 3,198,009 | 8/1965 | Fishman et al. ........... 73/211 |
| 3,207,372 | 9/1965 | Evans ....................... 222/67 |
| 3,216,418 | 11/1965 | Scislowicz ................ 128/214 |
| 3,227,173 | 1/1966 | Bernstein ................. 137/192 |
| 3,241,365 | 3/1966 | Schroeder et al. ......... 73/211 |
| 3,277,708 | 10/1966 | Reynolds et al. .......... 73/211 |
| 3,299,904 | 1/1967 | Burke ....................... 137/315 |
| 3,316,935 | 5/1967 | Kaiser et al. .............. 137/595 |
| 3,321,970 | 5/1967 | Walker, Sr. et al. ........ 73/211 |
| 3,340,871 | 9/1967 | Jellies ...................... 128/214 |
| 3,450,164 | 6/1969 | Walker, Jr. ................. 138/44 |
| 3,460,526 | 8/1969 | McKirdy et al. ........... 128/2.05 |
| 3,487,808 | 1/1970 | Perkins ..................... 116/117 |
| 3,498,316 | 3/1970 | Pinder et al. .............. 137/595 |
| 3,550,619 | 12/1970 | Halasz et al. .............. 137/595 |
| 3,604,420 | 9/1971 | Vallancourt ............... 128/275 |
| 3,605,496 | 9/1971 | Wenham ................... 73/202 |
| 3,626,938 | 12/1971 | Versaci ..................... 128/214 B |
| 3,667,464 | 6/1972 | Alligood, Jr. .............. 128/214 C |
| 3,677,248 | 7/1972 | McPhee ..................... 128/227 |
| 3,690,318 | 9/1972 | Gorsuch .................... 128/214 E |
| 3,756,233 | 9/1973 | Goldowsky ................ 128/214 C |
| 3,759,098 | 9/1973 | Logsdon et al. ............ 73/205 R |
| 3,785,378 | 1/1974 | Stewart .................... 128/214 C |
| 3,796,245 | 3/1974 | Wildensteiner ............ 150/1 |
| 3,803,914 | 4/1974 | Noiles ....................... 73/209 |
| 3,805,612 | 4/1974 | Shiba ........................ 73/211 |
| 3,807,397 | 4/1974 | Noiles ....................... 128/214 C |
| 3,826,137 | 7/1974 | Clarke ....................... 73/194 R |
| 3,838,599 | 10/1974 | Purtell ....................... 73/211 |
| 3,851,526 | 12/1974 | Drexel ...................... 73/202 |
| 3,851,668 | 12/1974 | Benjamin ................. 137/625.3 |
| 3,929,157 | 12/1975 | Serur ........................ 128/214 C X |
| 3,931,818 | 1/1976 | Goldowsky ................ 128/214 C |
| 3,938,539 | 2/1976 | Strouth et al. ............. 137/202 |
| 3,941,126 | 3/1976 | Dietrich et al. ............ 128/214 R |
| 3,949,745 | 4/1976 | Howell ...................... 128/214 C |
| 3,963,024 | 6/1976 | Goldowsky ................ 128/214 R |
| 3,967,620 | 7/1976 | Noiles ....................... 128/214 C |
| 3,998,097 | 12/1976 | Akashi et al. ............... 73/211 |
| 4,043,332 | 8/1977 | Metcalf ..................... 128/214 E |
| 4,056,100 | 11/1977 | Noiles ....................... 128/214 C |
| 4,079,737 | 3/1978 | Miller ........................ 128/214 R |
| 4,096,879 | 6/1978 | Serur et al. ................. 137/433 X |
| 4,099,527 | 7/1978 | Howell ...................... 128/214 C |
| 4,136,692 | 1/1979 | Goldowsky ................ 128/214 C |

*Primary Examiner*—Stephen C. Pellegrino
*Attorney, Agent, or Firm*—Kane, Dalsimer, Kane, Sullivan and Kurucz

[57] ABSTRACT

An indicator/controller for dispensing medical fluids (e.g., intravenously) is disclosed. The device has vented chambers that are movable vertically with respect to one another, thin-plate orifices, capillary chambers, and membrane valves, in addition to other features. The device need be set only once to the desired flow and it will maintain that flow rate regardless of changes in temperature or the height of fluid in the supply.

8 Claims, 14 Drawing Figures

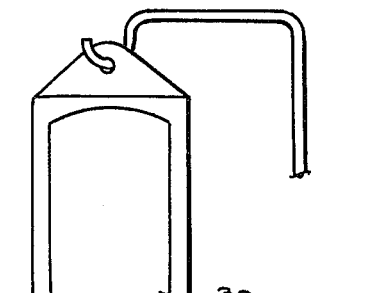
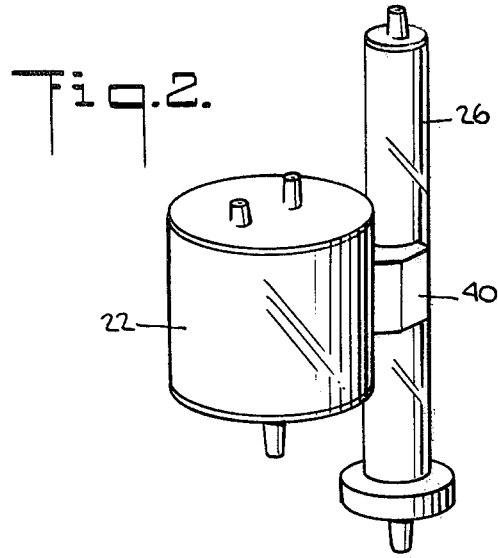
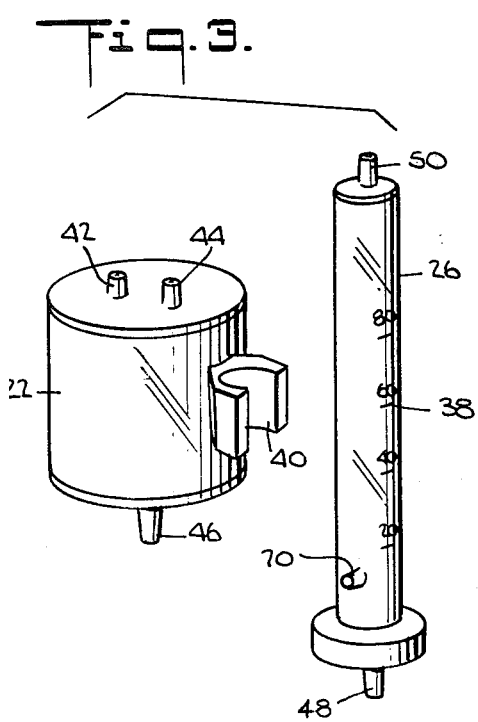
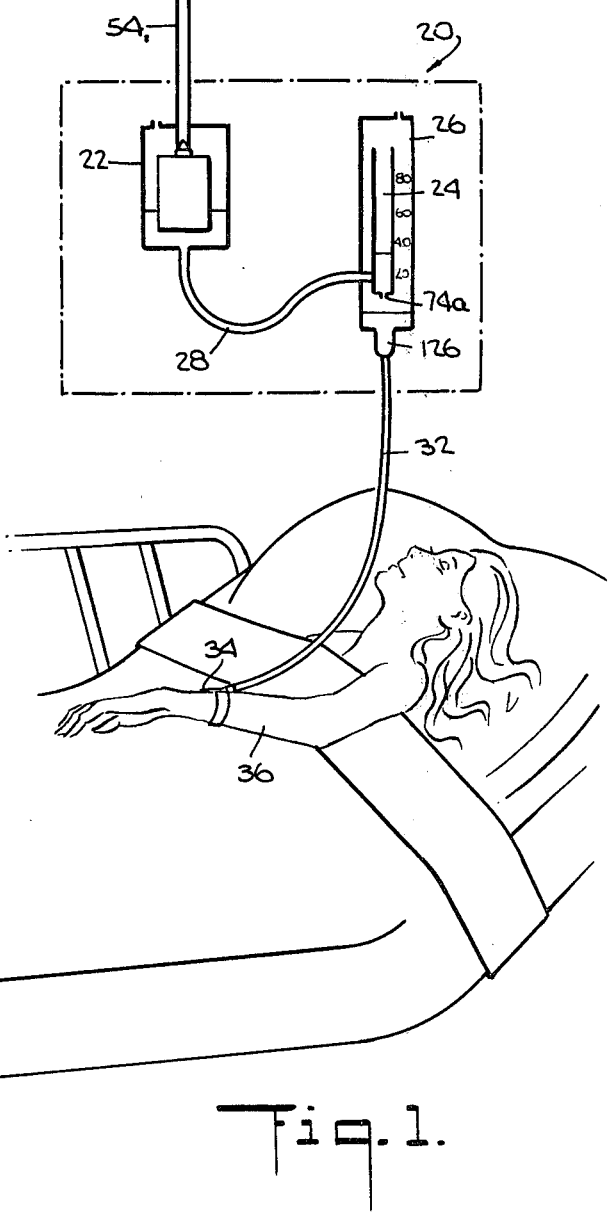

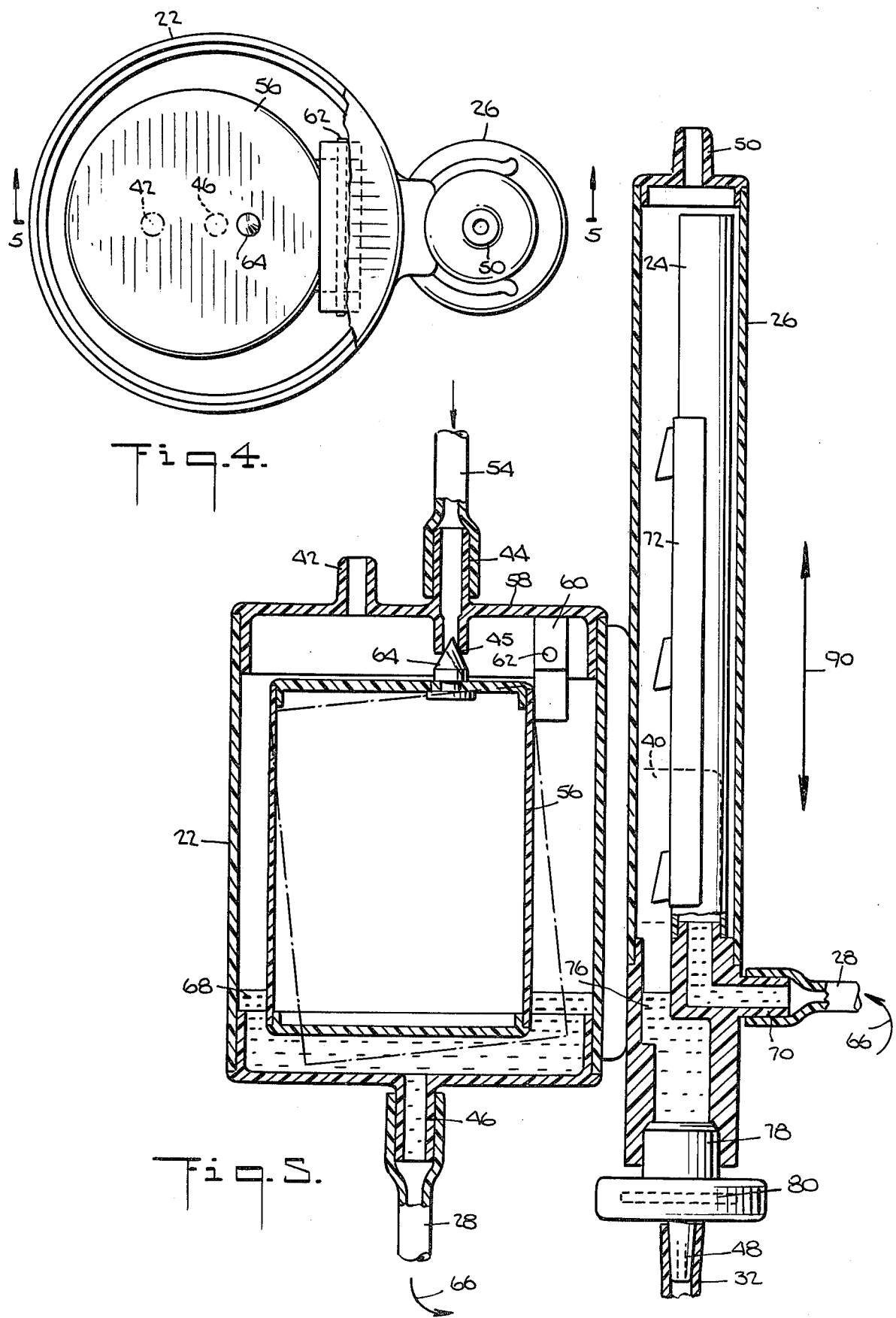

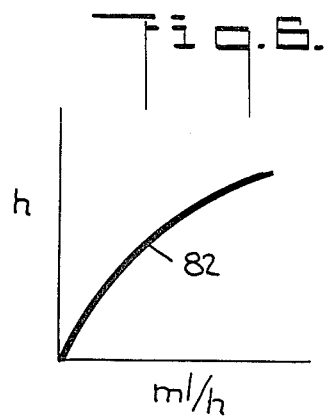
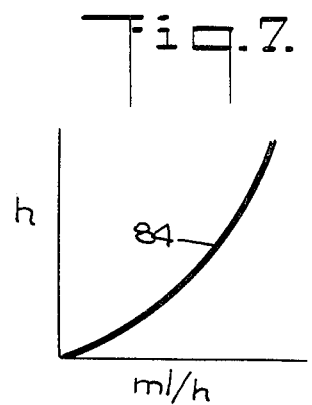
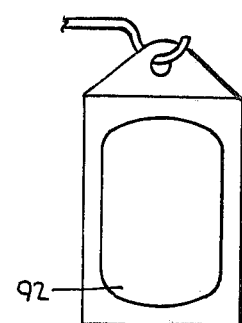
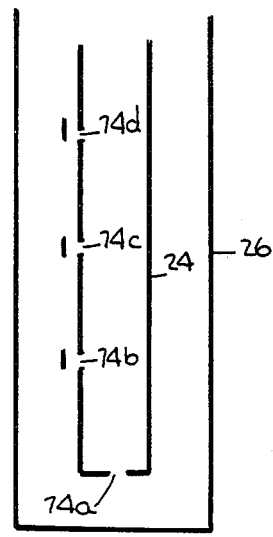
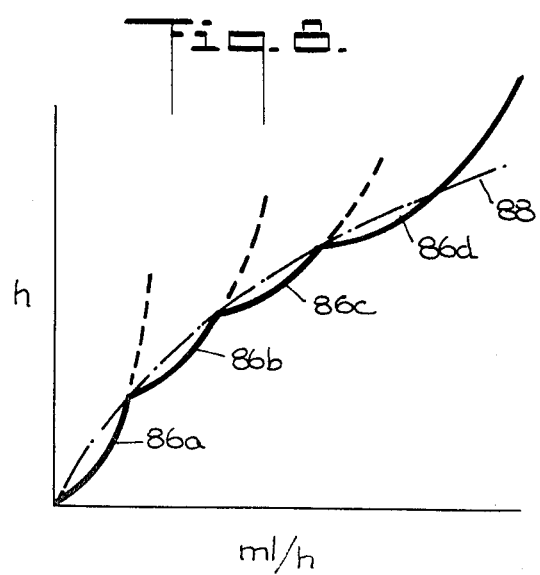
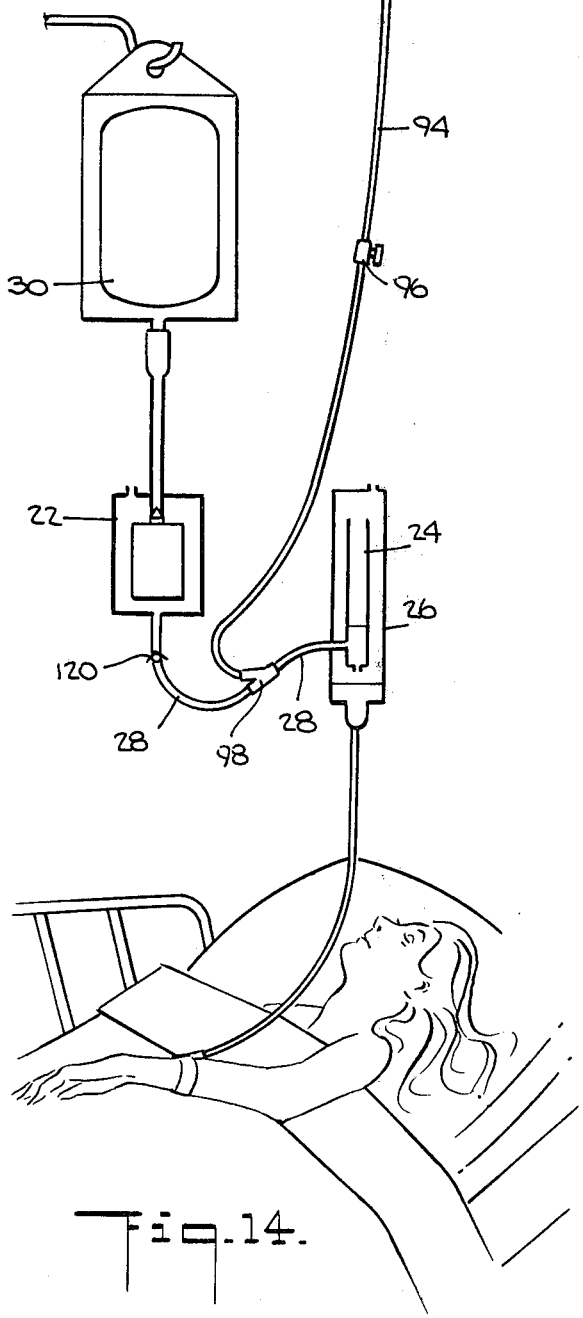

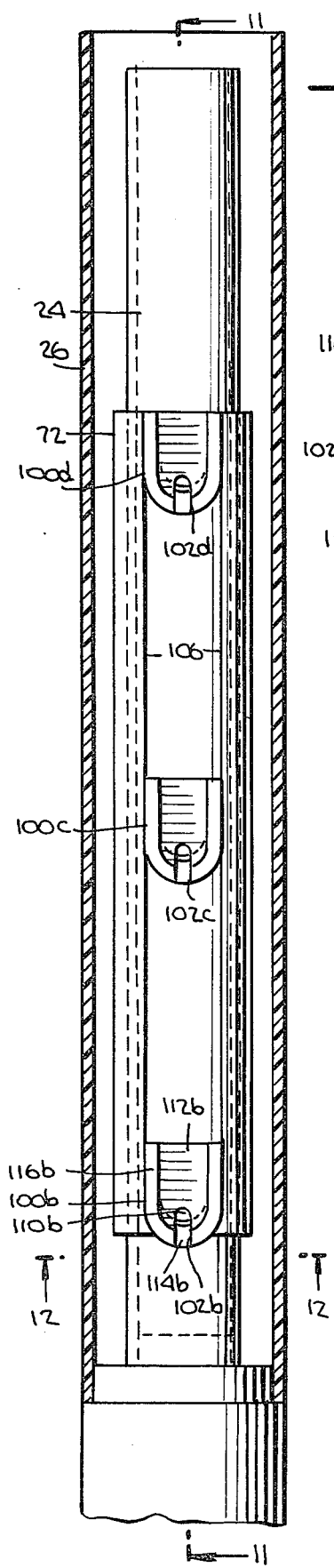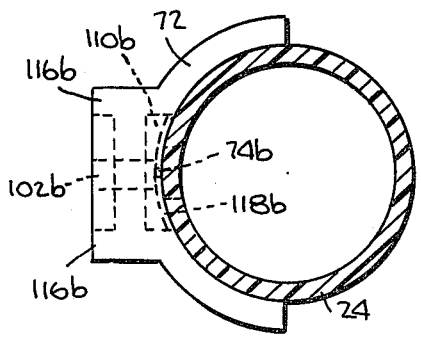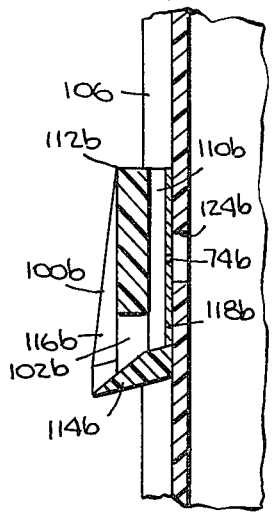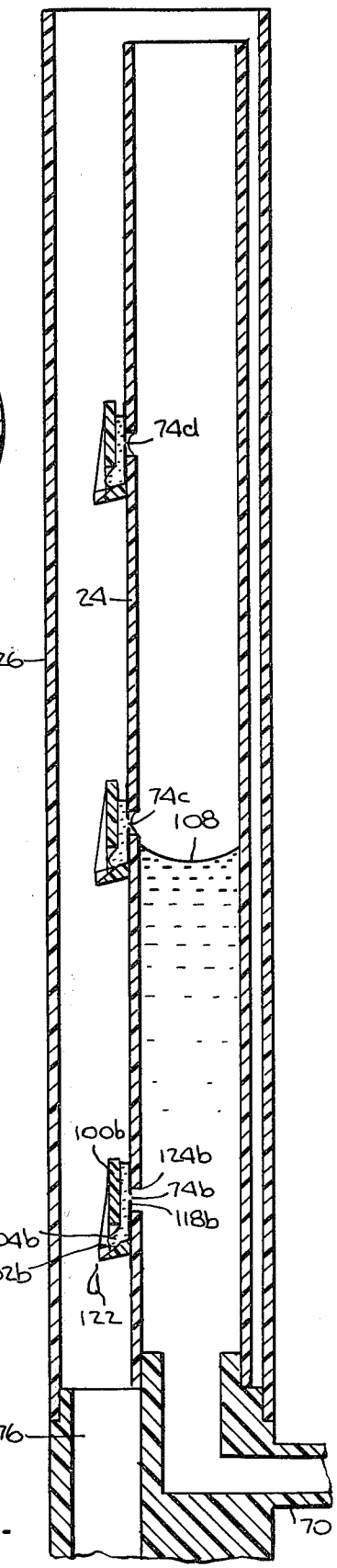

MEDICAL FLUID FLOW RATE INDICATING/CONTROLLING DEVICE

BACKGROUND OF THE INVENTION

Numerous devices have been suggested for use in administering medical fluids to patients. In particular, there have been numerous attempts to design a reliable, accurate intravenous flow rate indicator/controller that is inexpensive enough to be disposable.

Desirably, such a device should maintain the initially set rate of delivery even if the temperature changes and handle a wide range of fluids without being affected by the differences in viscosity. The device should be easy to prime, handle a wide range of flows, reset automatically to the desired primary flow rate after any secondary fluid delivery ends, and stop fluid delivery before air enters the tube leading from the device to the patient.

If a device can do those things, chances for a medical emergency caused by excessive or insufficient flow of medication or by an air embolism from the procedure are reduced. Additionally, demands on nursing time are lessened because frequent readjustment to the initially set flow rate is not needed and hospital costs are lowered since a hospital need keep only one type of device in stock to handle both pediatric and adult patients (the typical flow rates are significantly different) and all medical fluids normally dispensed (viscosities vary significantly).

The classic intravenous metering set comprises a fluid supply container (commonly of 1 liter volume), a drip chamber, tubing from the bottom of the drip chamber to a needle in the patient, and a device to pinch the tubing to control the flow. Fluid from the supply container drips into the chamber through a standard size cannula at a rate determined by the internal cannula fluid pressure and the gas-phase pressure in the chamber (controlled indirectly by pinching the tubing).

The cannulae are supposed to deliver a fixed number of drops per milliliter (typically 15, 20, or 60), and flow rate is set by pinching the tube to achieve a number of drops per unit time equivalent to the prescribed number of milliliters of medication per hour. However, cold-flow of the tubing material where pinched, which enlarges the cross-sectional flow path, and, in some systems, lowering of the fluid level in the supply container as fluid administration progresses may cause the flow rate to vary significantly from that initially set. Additionally, the flow rate usually will change with variations in the patient's venous pressure and vertical movement of the neddle's point of entry.

Numerous attempts have been made to provide metering devices that are calibrated to indicate the flow rate and are free from these problems. For example, U.S. Pat. Nos. 2,479,786, 3,340,871, 3,938,539, and 4,136,692 disclose devices for metering medical fluids where the flow rate is indicated by the height of the fluid in a chamber. The devices of the first three patents utilize apparatus having apertures in relatively thick walls through which the fluid passes. The fourth, U.S. Pat. No. 4,136,692, makes use of one or more thin-plate orifices, which it discloses are relatively insensitive to variations in fluid viscosity. Additionally, U.S. Pat. No. 3,690,318 discloses an intravenous administration device utilizing a plurality of orifices.

U.S. Pat. Nos. 3,756,233 and 3,931,818 disclose two-chamber intravenous metering devices in which the fluid flow rate is controlled by varying the relative height of the chambers. Additionally, U.S. Pat. No. 3,756,233 discloses venting the device to the atmosphere. The device of U.S. Pat. No. 3,931,818 makes use of tubing having a standard pressure drop to fluidly connect the two chambers.

U.S. Pat. Nos. 3,207,372, 3,227,173, and 3,963,024 disclose devices having float check valves to prevent air from entering the tubing leading from the device to the patient when the fluid in each device is exhausted. U.S. Pat. Nos. 3,967,620 and 4,056,100 discloses the use of hydrophilic material acting as membrane valves for the same purpose. Additionally, the devices of U.S. Pat. No. 3,963,024 utilize two fluid chambers that are gas-phase pressure-equalized.

However, none of these patents provides a reliable, accurate, low-cost intravenous fluid flow rate indicator/controller that is insensitive to ambient temperature, can maintain the initially set flow rate, is easy to prime, resets to the primary flow rate after any secondary fluid administration ends, and indicates flow rate over a wide range of flows, with particular sensitivity at very low flow rates and without regard to fuid viscosity.

SUMMARY OF THE INVENTION

An invention providing a device meeting these requirements has now been discovered. Broadly, the apparatus of this invention comprises:

(a) a first chamber vented to the atmosphere and having a liquid inlet in fluid communication with a liquid supply, a liquid outlet, and means to maintain the height of liquid in the chamber essentially constant;

(b) a second chamber vented to the atmosphere, in fluid communication with the liquid outlet of the first chamber for receiving liquid therefrom, and having a thin-wall orifice plate at a predetermined point, said plate having an orifice through which liquid received from the first chamber passes out of the second chamber, the height of liquid in the second chamber above the orifice indicating the flow rate through the orifice; and (c) means for setting the pressure on the liquid received from the first chamber just before the liquid passes through the orifice.

In a preferred embodiment the liquid flow rate indicating/controlling device of this invention comprises:

(a) a first chamber vented to the atmosphere and having a liquid inlet in fluid communication with a liquid supply, a liquid outlet, and float valve means movable vertically within narrow limits to maintain the height of liquid in the chamber essentially constant;

(b) a second chamber vented to the atmosphere, in fluid communication with the liquid outlet of the first chamber for receiving liquid therefrom, and having a thin-wall orifice plate at a predetermined point, said plate having an orifice through which liquid received from the first chamber passes out of the second chamber, the height of liquid in the second chamber above the orifice indicating the flow rate through the orifice;

(c) a third chamber vented to the atmosphere in which the second chamber is located, said third chamber having a liquid outlet through which liquid leaving the orifice from the second chamber passes to the patient and having a membrane outlet valve downstream of the orifice and upstream of the liquid outlet; and (d) means for setting the pressure on the liquid received from the first chamber just before the liquid passes through the orifice, comprising means to set the relative height of the first and second chambers.

Another aspect of the invention relates to a process for administering medical fluids to a patient utilizing the apparatus of this invention, said process comprising supplying fluid to the first chamber inlet, fluidly connecting the third chamber liquid outlet to the patient, and setting the relative heights of the first and second chambers for the desired flow.

BRIEF DESCRIPTION OF THE DRAWINGS

To facilitate further description of the invention, the following drawings are provided in which:

FIG. 1 shows an embodiment of the present invention used to control and indicate the flow of intravenous fluid to a patient;

FIG. 2 is a perspective view of an embodiment of this invention showing the chambers of the invention attached to one another at the required relative height to establish the desired flow rate;

FIG. 3 is a perspective view of the device showing the chambers separated;

FIG. 4 is a partially cut-away plan view of the configuration of FIG. 2;

FIG. 5 is a sectional view of the device of FIG. 4 taken along line 5—5;

FIG. 6 is a graph indicating the desired relationship between flow rate and height of a indicating level for an intravenous indicating/controlling device;

FIG. 7 is a graph showing the relationship between the flow rate through a thin-plate orifice and the height of fluid above the orifice;

FIG. 8 schematically illustrates a device according to the present invention wherein a plurality of thin-wall orifices are used to mimic the desired curve of FIG. 6;

FIG. 9 shows the height-flow rate curve for the device of FIG. 8;

FIG. 10 is a front elevational view of a device similar to that shown in FIG. 8 but having three sidewall orifices and no bottom orifice;

FIG. 11 is a side elevational view of the device taken along line 11—11 of FIG. 10;

FIG. 12 is a cross-sectional view of the device taken along line 12—12 of FIG. 10;

FIG. 13 is a detail side elevational view of the lowest of the side-wall orifices and its associated capillary chamber; and FIG. 14 shows the administration of fluid from a secondary set utilizing the device of FIG. 1.

It should be understood that these drawings are provided for illustrative purposes only and should not be construed to limit the scope of the invention. It should also be understood that for the sake of clarity, elements shown in one view may not be shown in another.

DETAILED DESCRIPTION OF THE INVENTION

FIG. 1 shows the administration of intravenous fluid to a patient using one embodiment of the present invention, shown within the dotted lines, generally indicated by reference numeral 20. Intravenous fluid flows from conventional fluid supply bag 30 via tube 54 into first chamber 22. The liquid then passes through tube 28 into second chamber 24 near its bottom. Second chamber 24 is rigidly mounted within third chamber 26 and fluid leaving the second chamber through orifice 74a falls to the bottom of third chamber 26, having conventional drip chamber 126. Tube 32 leads the fluid from drip chamber 126 to needle 34, located within arm 36 of the patient.

Second chamber 24 is open at its top and since third chamber 26 is vented to the atmosphere, second chamber 24 is subjected to atmospheric pressure. The fluid inside first chamber 22 is likewise subjected to atmospheric pressure through its vent. Both vents contain hydrophobic filters to prevent liquid from passing through the vents and to prevent air-borne contaminants from entering through the vents.

FIG. 2 shows third chamber 26 mounted on first chamber 22 by means of retaining clip 40. Chamber 26 may be moved vertically within clip 40 to vary the desired flow rate.

In FIG. 3, flow rate indicia 38 are located on the wall of third chamber 26. Indicia 38 are typically in units of milliliters per hour and are located at heights corresponding to the indicated flows through the one or more thin-plate orifices used herein. First chamber 22 is equipped with fluid inlet 44, fluid outlet 46, and vent 42. Third chamber 26 has liquid outlet 48, vent 50, and liquid inlet 70.

FIG. 4 is an overhead view, showing float 56 (described below) located within first chamber 22.

FIG. 5 is a partial sectional view of the device. Fluid in tube 54 from the supply enters first chamber 22 through inlet 44 and flows out of the chamber through liquid outlet 46, through tube 28 and into third chamber 26 through inlet 70, as indicated by arrows 66. The level of liquid 68 inside first chamber 22 is maintained within narrow limits by a float valve comprising float 56 and conical portion 64. The float is hingedly connected to top wall 58 of chamber 22 by hinge 60, which allows the float to rotate about pin 62.

When fluid 68 rises to the desired level, float 56 rests on the fluid in the position shown in solid lines, thereby forcing conical portion 64 into valve seat 45 to prevent additional liquid from entering the chamber. When the liquid level falls, the float rotates downward, moving conical portion 64 down (as shown by the dotted lines) to admit additional fluid and raise the fluid back to the desired level.

Fluid enters third chamber 26 through inlet 70. Located within the third chamber is second chamber 24, which is open at the top and is, therefore, open to atmospheric pressure via vent 50. The vertical adjustability of chambers 24 and 26 with respect to first chamber 22 is indicated by arrow 90.

Fluid entering second chamber 24 through inlet 70 leaves that chamber through one or more orifices in thin-wall orifice plates, none of which is visible in this figure. The fluid is maintained by back-pressure at a height above each particular orifice depending on the liquid velocity through that orifice. For an orifice in an orifice plate having zero thickness, the velocity of flow through the orifice is directly proportional to the square root of the height of liquid above the orifice, independent of fluid viscosity.

It has been found that orifices in plates of no more than approximately 0.003 inches (0.076 mm) in thickness display the same characteristics within the degree of accuracy required for medical fluid administration. Accordingly, it is preferred that the thin-wall orifice plates of this invention be no more than approximately 0.003 inches (0.076 mm) thick.

The flow capacity of tube 54, inlet 44, valve seat 45, outlet 46, tube 28, and inlet 70 is very large compared to that of the orifice flow-controlling system of second chamber 24. Therefore, constant liquid heads above the one or more orifices are maintained by the first chamber liquid feeding system and are not diminished by the flow through the one or more orifices employed in second chamber 24.

Fluid discharged through the one or more orifices falls into bottom chamber 76 from which it flows through discharge fitting 78 connected to liquid outlet 48. A thin sheet of hydrophilic material 80 is located within fitting 78. This material when wet passes liquid but will not pass air, assuming the break-through air pressure (or bubble point) is not reached. Material 80 is a membrane valve, allowing the liquid level to fall to the top surface of the valve but no farther. Accordingly, it prevents air from entering nozzle 48 or tube 32, which could cause an air embolism if the air entered the patient.

Curve 82 of FIG. 6 indicates the desired relationship between flow rate and height above an orifice for an intravenous indicating/controlling device. Such a device would be most sensitive at low flow rates, that is, a large change in the height of the liquid column at low flow rates would indicate a relatively small change in flow rate but the same change in height at a high flow rates would indicate a large change in flow rate. That is desirable because in such a device small changes in flow rate at low flow rates (as for pediatric care) are more easily discernible but the device also can be used to indicate high flow rates. Such a device would have an essentially constant percentage error in indication (readability) and control over the entire flow range, e.g., plus or minus 5-10%.

Curve 84 of FIG. 7 has the opposite sensitivity. At low flow rates a small change in height (which may be difficult to observe) indicates a large change in flow rate and at high flow rates the same change in height indicates a relatively smaller change in flow rate. That is undesirable since changes in flow at low flow rates are not easily discerned and a long column is required to accommodate the large range of flow rates needed. The shape of curve 84 shows the classic relationship between liquid flow rate through an orifice and liquid head height above it, namely, flow rate is proportional to the square root of the fluid height.

FIG. 8 shows a solution in accordance with the present invention to the problem posed by the opposite shapes of curves 82 and 84. A plurality of thin-plate orifices 74 are utilized along the length of second chamber 24. This allows the device to enjoy the benefits of using thin-plate orifices and yet display the sensitivity of curve 82, as will be described.

FIG. 9 illustrates the four curves 86 for each of the four orifices 74. Since the total flow of fluid out of third chamber 26 is the sum of flows through the four orifices, the four curves 86 are additive in the manner shown. Specifically, curve 86a illustrates the fluid height/flow rate relationship for orifice 74a. Curve 86b has as its own origin zero flow through it at the height at which fluid reaches the orifice 74b, and so forth. Accordingly, the composite curve (the solid-line portions of curves 86a, b, c, and d) mimics the shape of desired curve 88 (having the same shape as curve 82 of FIG. 6).

The device of FIGS. 8 and 9 utilizes four orifices, one at the bottom and three at the side. The device shown in FIGS. 10 to 13 dispenses with the bottom orifice for ease of manufacture. The number and placement of orifices in accordance with this invention is a matter of design choice.

FIG. 10 is a front elevational view of second chamber 24 within third chamber 26. Attached to second chamber 24 is capillary chamber plate 72 comprising capillary chambers 100b, c, and d attached to vertical members 106. These chambers are used to eliminate possible errors caused by the use of sidewall orifices 74b, c and d (FIG. 8), as will be described.

Turning to FIG. 11, fluid from first chamber 22 (not shown) enters second chamber 24 through inlet 70, flows through the appropriate entrances 124, and then flows through the respective orifices in metal foil 118. Without capillary chambers 100 fluid level 108 would have to rise some distance above a sidewall orifice before flow through that orifice could commence. (That is due to some finite pressure head of liquid being required to overcome the liquid's surface tension on the inlet side of each orifice and wet the orifice to allow flow through it.) Indicia 38 on third chamber 26 (FIG. 3) would then indicate a higher than actual flow rate since fluid level 108 would be above the orifice without causing any flow through the orifice until the pressure head necessary to overcome the surface tension had been achieved. Furthermore, the surface tension pressure may vary with the degree and timing of the wetting of the surfaces involved. Therefore, it is variable and not subject to correction by calibration. That is especially true for small orifices, on the order of 0.010 inches (0.25 mm) in diameter.

Accordingly, the purpose of capillary chambers 100 is to maintain small reservoirs of fluid 104 on the discharge side of each orifice so that fluid flow through each orifice commences as soon as the liquid level reaches it. Even if the liquid height in chamber 24 falls below one or more of orifices 74d, c, and b, capillary chambers 100d, c, and b remain filled due to capillary action and surface tension. If the fluid again rises in chamber 24 to a higher orifice, flow through that orifice starts immediately because the orifice is primed by the liquid in the respective capillary chamber outside the orifice. Liquid drops 122 fall from each of the capillary chambers into liquid pool 76, from which the liquid flows to the patient.

Referring now to FIGS. 10 to 13, the construction of the capillary chamber is as follows (only chamber 100b will be described since the other two are essentially identical). Liquid discharged through orifice 74b in metal foil 118b passes into vertical passageway 110b, through archway-shaped slot 102b, and on to the end of bevelled bottom member 114b, from which it falls. The front plate of the chamber comprises plate 112b, of uniform thickness, in which slot 102b is located, and U-shaped raised ridge 116b. In FIG. 10, the bevelled surface of bottom member 114b is visible through slot 102b.

As will be understood by one skilled in the art, the liquid in capillary chambers 100 will rise above the orifices to a degree depending on the width of the vertical passageway 110 and the surface tension of the liquid. At some height within vertical passageway 110, the hydrostatic pressure is atmospheric, since the pressure inside the liquid at the top of passageway 110 is below atmospheric (due to surface tension causing a meniscus) and the pressure on the liquid near the bottom slot is above atmospheric (due to the head of liquid in the passageway). Each capillary chamber should be located so that the point of atmospheric pressure is at the same height as its respective orifice. For a device having the dimentions given below, that point is approximately half-way up the vertical passageway.

FIG. 14 shows administration of fluid from a secondary set using one embodiment of this invention. Secondary fluid flows from supply 92 through tubing 94 into Y-connection 98, into tube 28, through second chamber 24, and out of third chamber 26 into the patient. Supply 92 is placed at a height above primary supply 30, and check valve 120 may be provided to aid in preventing the secondary fluid from entering first chamber 22. Even without check valve 120, only a limited amount of secondary fluid enters first chamber 22 because float 56 prevents reverse flow up into primary supply 30 and the hydrophobic material in vent 42 will not pass liquid. The flow rate of secondary fluid is controlled by conventional squeeze clamp valve 96 and indicated by chamber 24.

Typically, primary fluid (supply 30) is administered at flow rates ranging from just a few milliliters per hour up to 100 or more milliliters per hours, whereas the total volume of secondary fluid introduced is often no more than 50 milliliters but must be introduced at higher flow rates. Because the device of this invention indicates a wide range of flow rates, the flow rate of the secondary fluid may be indicated by second chamber 24. Additionally, when the secondary fluid is exhausted, the device automatically restarts primary fluid flow at the previously set primary rate. That occurs because metering of the secondary fluid does not require changing the relative height of chambers 22, 24, and 26 and without the secondary fluid flowing from supply 92, check valve 120 can reopen. Primary fluid can not flow up into secondary supply 92 since supply 92 is at a height above primary supply 30.

Typical dimensions for the device are as follows. First chamber 22 is approximately 2.5 inches (63 mm) in outer diameter and 3 inches (76 mm) high, with a wall thickness of ⅛ inch (3 mm). Connections 44 and 46 and vent 42 are approximately 0.22 inches (6 mm) in outer diameter. Float 56 maintains the liquid level in first chamber 22 at a constant height of about 2 inches (51 mm) plus or minus 0.04 inches (1.0 mm) above the chamber bottom.

Second chamber 24 is approximately ⅜ inch (9.5 mm) in inner diameter and 5 inches (127 mm) high, with a wall thickness of 0.04 inch (1 mm). Third chamber 26 is 0.8 inches (20 mm) in outer diameter and 6 inches (152 mm) long, with a wall thickness of 0.04 inches (1 mm).

The thickness of metal foil 118 is approximately 0.003 inches (0.076 mm), with orifice diameters of from 0.008 to 0.020 inches (0.2 to 0.5 mm), depending on the flow rate to be measured. For the device of FIGS. 10 to 14, orifice diameters of 0.007 inches (0.18 mm), 0.010 inches (0.25 mm), and 0.015 inches (0.38 mm) for orifices 74b, c, and d, respectively, are suitable for indication/control of fluid flow rates of from 0 to 250 milliliters per hour.

The width of the capillary chamber (FIG. 13) is approximately 0.06 inches (1.5 mm), with a height of 0.8 inches (20 mm). The width of vertical wall 112b and bottom member 114b at its widest is approximately 0.06 inches (1.5 mm) and the equivalent diameter of slot 102b is from 0.06 to 0.09 inches (1.5 to 2.3 mm).

The device may be made of any pharmacologically suitable material. For the first, second, and third chambers the materials preferably are transparent. Typical materials for them are styrene, styrene-acrylonitrile, and polypropylene. Connecting tubing typically will be polyvinyl chloride. The orifice plates (metal foil) typically will be of type 302 or 316 stainless steel. The membrane valve will be hydrophilic material.

The device is utilized by connecting the first chamber to a supply of fluid. If this is the first supply to be connected to the device, the second and third chambers are lowered sufficiently so that fluid overflows the top of the second chamber and falls into the third chamber. That wets the membrane filter, which then acts as a membrane valve, allowing liquid but not air to leave the third chamber, and causes flow through all orifices and priming and filling of all capillary chambers. The tube from the bottom of the third chamber to the patient is allowed to fill with fluid and is connected to the patient in the known manner. The relative height of the chambers is then adjusted to dispense the fluid at the flow rate indicated by indicia 38 (FIG. 3).

Because the fluid level in the first chamber is maintained within narrow limits, the hydrostatic pressure on the fluid passing through the one or more orifices of known height and size in the second chamber is maintained within narrow limits. The use of thin-plate orifices makes the device insensitive (within the accuracy required) to differences in fluid viscosity. Venting the chambers to the atmosphere prevent changes in the gas-phase pressure in the chambers that could significantly affect the liquid flow rate.

As a result of these features, the device may be pre-calibrated so that given fluid heights in the second chamber indicate specific, reproducible flow rates. The chambers need be adjusted only once to the relative height shown by the indicia to produce the prescribed flow rate. The fluid will be dispensed at the indicated flow rate no matter which medical fluid is metered, how much liquid remains in the supply, or how the temperature changes.

So long as metering chamber 26 and its outlet membrane valve 80 are sufficiently high above the patient's vein that the pressure at 34 (FIG. 1) due to liquid in tube 32 exceeds the patient's venous pressure at that point plus the pressure drop in tube 32 and its connections at the instant rate of flow, all fluid delivered to fitting 78 and membrane valve 80 will be delivered through tube 32 to the patient. No more fluid can be delivered to the patient than is permitted to flow through the metering system. Therefore, the present flow rate will obtain as long as fluid is delivered from supply 30. In an emergency or during another event that requires a flow rate greater than the metering system permits, first chamber 22 can be raised sufficiently high to cause fluid to overflow the top of second chamber 24 and deliver fluid at rates up to 2000 milliliters/hour.

As will be obvious to one skilled in the art, variations and modifications may be made in the embodiments described and the claims are intended to cover all modifications and variations as fall within the true spirit and scope of this invention.

I claim:

1. A liquid flow rate indicating/controlling device comprising:
   (a) a first chamber vented to the atmosphere and having a liquid inlet in fluid communication with a liquid supply, a liquid outlet, and means to maintain the height of liquid in the chamber essentially constant;

(b) a second chamber vented to the atmosphere, in fluid communication with the liquid outlet of the first chamber for receiving liquid therefrom, and having a thin-wall orifice plate at a predetermined point, said plate having an orifice through which liquid received from the first chamber passes out of the second chamber, the height of liquid in the second chamber above the orifice indicating the flow rate through the orifice; and (c) means for setting the pressure on the liquid received from the first chamber just before the liquid passes through the orifice.

2. The device of claim 1 wherein the means for setting the pressure on the liquid comprises means to adjust the relative height of the two chambers.

3. The device of claim 1 wherein the means to maintain the height of the liquid in the first chamber essentially constant comprises float valve means movable vertically within narrow limits.

4. A liquid flow rate indicating/controlling device for administration of medical fluids to a patient, said device comprising:

(a) a first chamber vented to the atmosphere and having a liquid inlet in fluid communication with a liquid supply, a liquid outlet, and float valve means movable vertically within narrow limits to maintain the height of liquid in the chamber essentially constant;

(b) a second chamber vented to the atmosphere, in fluid communication with the liquid outlet of the first chamber for receiving liquid therefrom, and having a thin-wall orifice plate at a predetermined point, said plate having an orifice through which liquid received from the first chamber passes out of the second chamber, the height of liquid in the second chamber above the orifice indicating the flow rate through the orifice;

(c) a third chamber in which the second chamber is located, said third chamber having a liquid outlet through which liquid leaving the orifice from the second chamber passes to the patient; and (d) means for setting the pressure on the liquid received from the first chamber just before the liquid passes through the orifice.

5. The device of claim 4 wherein the means for setting the pressure on the liquid comprises means to set the relative heights of the first and second chambers.

6. The device of claim 4 wherein a membrane outlet valve is located in the third chamber upstream of the third chamber liquid outlet and downstream of the orifice.

7. A liquid flow rate indicating/controlling device for administration of medical fluids to a patient, said device comprising:

(a) a first chamber vented to the atmosphere and having a liquid inlet in fluid communication with a liquid supply, a liquid outlet, and float valve means movable vertically within narrow limits to maintain the height of liquid in the chamber essentially constant;

(b) a second chamber vented to the atmosphere, in fluid communication with the liquid outlet of the first chamber for receiving liquid therefrom, and having a thin-wall orifice plate at a predetermined point, said plate having an orifice through which liquid received from the first chamber passes out of the second chamber, the height of liquid in the second chamber above the orifice indicating the flow rate through the orifice;

(c) a third chamber vented to the atmosphere in which the second chamber is located, said third chamber having a liquid outlet through which liquid leaving the orifice from the second chamber passes to the patient and having a membrane outlet valve downstream of the orifice and upstream of the liquid outlet; and (d) means for setting the pressure on the liquid received from the first chamber just before the liquid passes through the orifice comprising means to set the relative height of the first and second chambers.

8. A process for administering medical fluid to a patient utilizing the device of claim 7, said process comprising supplying the fluid to the first chamber inlet, fluidly connecting the third chamber liquid outlet to the patient, and setting the relative heights of the first and second chambers for the desired flow.

* * * * *